United States Patent [19]

Matsutani

[11] Patent Number: 5,353,624
[45] Date of Patent: Oct. 11, 1994

[54] CRIMPING APPARATUS FOR ATTACHING A SUTURE TO A EYELESS NEEDLE

[75] Inventor: Kanji Matsutani, Tochigi, Japan

[73] Assignee: Kabushiki Kaisha Matsutani Seisakusho, Tochigi, Japan

[21] Appl. No.: 9,114

[22] Filed: Jan. 26, 1993

[30] Foreign Application Priority Data

Jan. 27, 1992 [JP] Japan .................. 4-034025

[51] Int. Cl.5 .................. B21G 1/00; B23P 11/00
[52] U.S. Cl. .................. 72/413; 72/416; 29/243.517; 163/1
[58] Field of Search .................. 72/416, 412, 470, 448, 72/413; 29/243.517, 243.5; 163/1, 5

[56] References Cited

U.S. PATENT DOCUMENTS

| 478,631 | 7/1892 | Parkinson | 72/413 |
| 3,263,479 | 8/1966 | Johnson | 72/416 |
| 3,842,651 | 10/1974 | Shaffer | 72/416 |
| 4,140,001 | 2/1979 | Moulton | 72/416 |
| 4,306,433 | 12/1981 | Matsutani . | |
| 4,799,311 | 1/1989 | Matsutani | 163/1 |

FOREIGN PATENT DOCUMENTS

325414 2/1930 United Kingdom .................. 72/412

Primary Examiner—Daniel C. Crane
Attorney, Agent, or Firm—Townsend & Banta

[57] ABSTRACT

A crimping apparatus for crimping a root end of an eyeless needle to fix a medical suture between an upper mold and lower mold. This apparatus comprises a swing arm disposed in parallel with the root end of the eyeless needle and the upper mold fixed to the swing arm. This apparatus also comprises a pivoting axis of the swing arm, being long enough to a crimping length of the eyeless needle. This pivoting axis is disposed far enough from the upper mold.

6 Claims, 6 Drawing Sheets

FIG. 7

CRIMPING APPARATUS FOR ATTACHING A SUTURE TO A EYELESS NEEDLE

FIELD OF THE INVENTION

This invention relates to a crimping apparatus used in a case of attaching a suture to a eyeless needle, and especially this apparatus is for a minute eyeless needle.

DESCRIPTION OF THE PRIOR ART

As a medical needle, usually an eyeless needle having a thickness of 0.14 mm–1.40 mm is used, which has a sharp needle point at one end and a hole to hold a suture at the other end (a root end). By inserting an end of a suture to the hole of the eyeless needle and crimping the root end by a crimping apparatus, a suture is attached to the eyeless needle.

When attaching the suture to the eyeless needle, the crimped root end must not have a shape to increase a penetrating resistance, and at the same time it is required for such a medical needle that a drawing-out load of the suture (the maximum load for the eyeless needle to hold the suture when pulling it) are within the stable range.

U.S. Pat. No. 4,306,443 to Matshutani discloses a crimping apparatus having a mechanism for adjusting a crimping pressure, which comprises a lower mold fixed to a frame and upper mold fixed to an end of a ram. This ram is coupled to a swinging arm at its mid-point and the swing arm is connected to a pivot on the frame at one end. At the other end (a swinging end) of the swing arm, a cam is disposed to contact a block at its bottom. The block is coupled with the swinging end of the swing arm. Thus, by rotating the cam, the swing arm is pushed and pulled, and the ram goes up and down along a guiding groove. When the ram goes down, the upper mold contacts the lower mold to crimp the root end of the eyeless needle, where the crimping pressure is adjusted by changing a distance form the pivoting point of the ram and the block, as well as by adjusting the pressure adjusting pin which comprises a insulating spring.

In this situation, when crimping a large number of such minute needles, by using the current apparatus mentioned above, the shape and diameter of the root end of the needle is not stable enough. Due to the aperture, the upper mold may shift and contacting point of the upper mold and the lower mold is scattered. When the eyeless needle is thick enough, this aperture can be neglected. But in the case of the micro needle, the apparatus cannot crimp it because the aperture is relatively bigger than the diameter of the needle.

Adding to that problem, the apparatus makes the block go up and down for the rotation of the cam. Because a distance between the block and the pivot spring are fixed constant, and because a contacting area between the block and a receiver of the pressing arm changes, as well as a contacting area between the swing arm and the pivot changes; the sliding resistance of the swinging arm also periodically changes in each cycle of the cam's rotation. Thus, even if setting a pressure of the upper mold, the crimping pressure changes in respect with the frictional resistance, then the apparatus cannot crimp the micro needle with constant pressure. In case of crimping a regular eyeless needle, because the required pressure is relatively larger than the pressure for crimping a micro needle, the unstabilization could be neglected. But in a case of crimping a micro needle, the required pressure is only 0.5 kg–1.0 kg, and a pressure must be finely controlled in a small range. Thus the changing of sliding resistance makes it more difficult to control the pressure of the upper mold.

SUMMARY OF THE INVENTION

The object of this invention is to provide an apparatus which can finely and constantly crimp even a micro needle. After studying, the inventor found conditions to crimp the micro needles having a consistent thickness of 23 μm~27 μm. The conditions are as follows:

(1) improving contacting accuracy of the moving and static molds.

(2) reducing sliding area of the moving part to minimize a frictional resistance.

To achieve those conditions, the mechanism used to make two molds contact finely uses a swinging arm having a small sliding section for the mechanism.

A crimping apparatus for eyeless needle of this invention has a static mold fixed on a frame of the apparatus and a upper mold coupled at a swing arm, which is disposed to be parallel to the root end of the needle. The swing arm is pivoted at a point which is far enough from the swinging end where the upper mold is fixed. Namely, the length between swinging end of the swinging arm and the pivoting axis is long enough, compared to a crimping length Lc (shown in FIG. 5), which is a length of a hole at the root end of the needle. The arm is pivoted at the frame or another supporting base. Thus, by rotating the swinging arm, one mold and the other mold contact and separate. Because of the rotating mechanism, a relative discrepancy of the molds is reduced. The sliding area between the swing arm and its pivot is small and contacting accuracy is not influenced much by the space between the swing arm and its pivot.

There are two kinds of discrepancies influencing the contacting accuracy of the molds; a twisting discrepancy and a parallel discrepancy. The twisting discrepancy is a discrepancy of a direction that a pivoting axis of the swing arm crosses the pre-set axis. The parallel discrepancy is a discrepancy that the pivoting axis parallel shifts against the pre-set axis. In this discrepancy one mold miscontacts the other mold in the direction perpendicular to the pre-set axis.

The twisting discrepancy and parallel discrepancy can be made small by reducing the space between a pivoting axis and its supporting member by choosing shapes of the pivoting axis and the supporting member or by improving processing accuracy thereof. For example, by choosing a transition fit of an interference fit for a contact of the pivoting axis and the bearing). Although a frictional resistance becomes big when making the space between the pivoting axis and its support minimum, the contacting accuracy of the molds is improved.

Figure 2A:
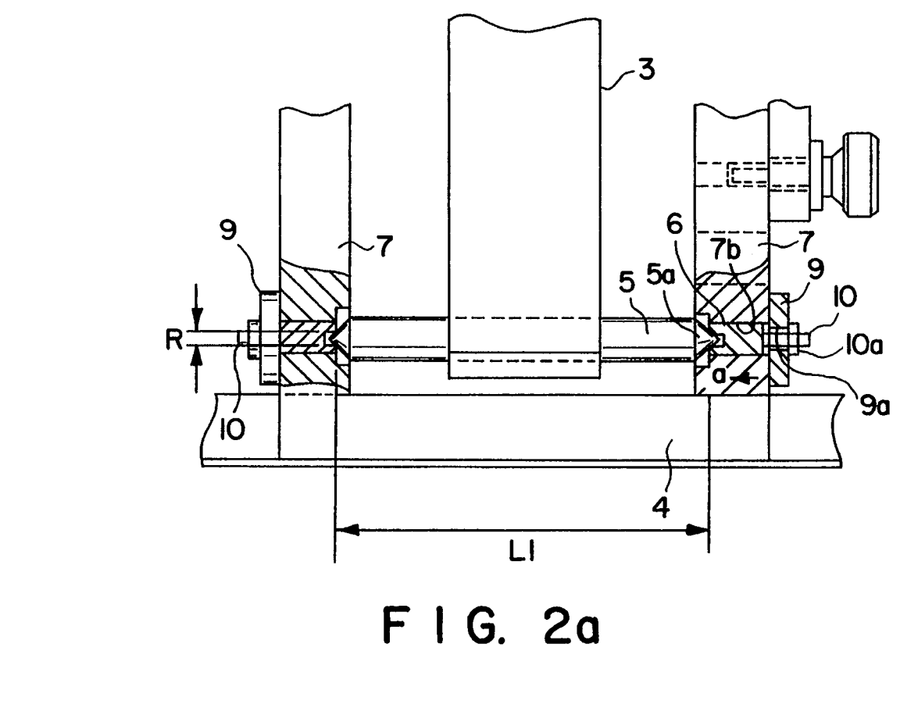
FIG. 2a shows a mechanism to support a swing arm according to the present invention.

Because the pivoting axis has a length L1 (shown in FIG. 2) which is long enough for the crimping length Lc (shown in FIG. 5), it makes the twisting discrepancy small. Therefore, in this invention, the twisting discrepancy doesn't have a big influence on the contacting accuracy of the molds which improves the crimping accuracy. Besides that, even though force in a direction of the root end of a needle is taken on the swing arm during operation of the crimping apparatus (like changing a mold, or maintaining the apparatus), the arm supporter can handle power to maintain contacting accuracy.

Figure 3:
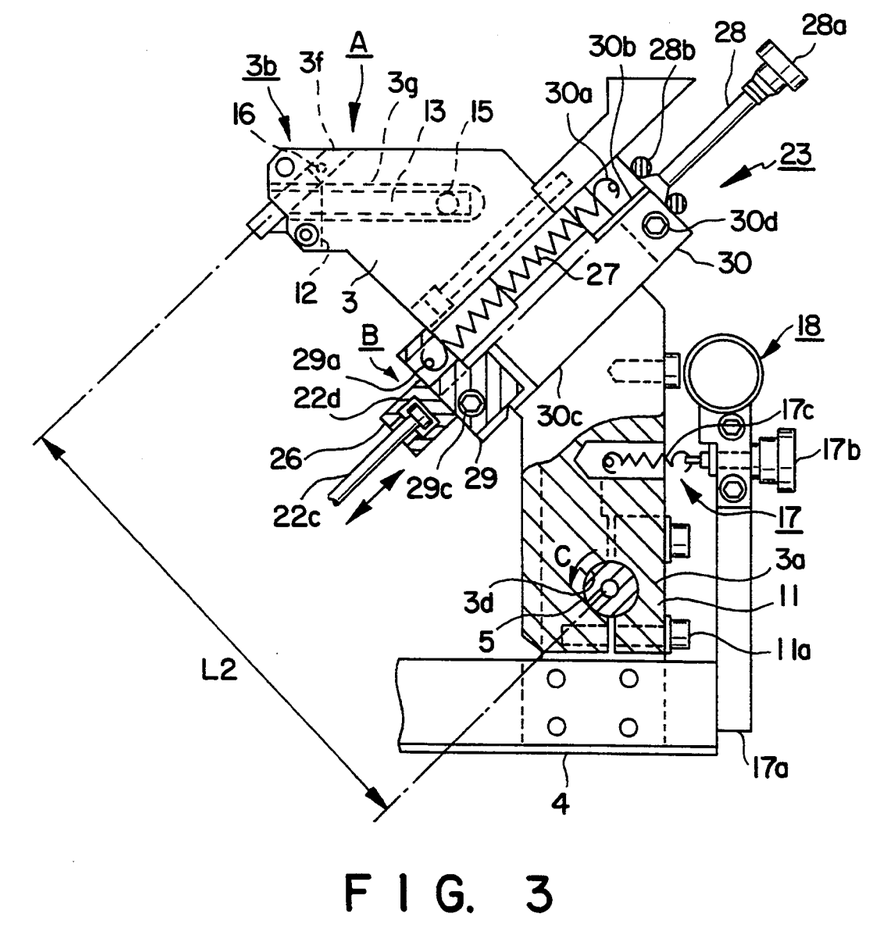
FIG. 3 is a sectional side view of swinging arm according to the present invention.

The ratio of the radius R against the distance L1 (R/L2) can be made small. When the distance L2 (shown in FIG. 3) between the pivoting axis of the swing arm and the contacting point of the molds is made long enough, by setting the radius R of the pivoting axis relatively small compared to the distance L2, the ratio of the radius R against the distance L2 (R/L2) can be small. This means that even if frictional resistance FR between the pivoting axis and the bearing is big, the influence on the rotation given by this resistance FR, FR*R/L2, can be kept small. If a force F is given to the swing arm for crimping the needle, the actual force to the swing arm becomes F-FR,R/L2. Because the ratio R/L2 is small, the influence of the frictional resistance FR against a crimping force, which works on the moving mold, can be ignored. Thus, this apparatus can give a stable force on the upper mold and it gets a good yield. The frictional resistance F has two kinds of resistance, namely static resistance and dynamic resistance. Because the frictional resistance F itself is small, the differences between those two resistances can be ignored, too.

One apparatus of this invention has a motor gear for moving the swinging arm, and a pressure setting means, which comprises a spring and an initial elasticity setting member, which is disposed between a swinging arm and the motor gear. The swinging arm is moved by the motor gear with the initial friction setting member to stabilize the pressure to the mold. In other words, by adjusting the pressure setting member to an initial friction pressure equal to a crimping pressure plus a frictional resistance between a pivoting axis and its bearing, when the mold contact each other, a micro needle can be crimped with proper pressure.

The apparatus of this invention also has a pressure adjustment member which can change its setting position at any place on the swing arm. Thus, it can easily increase or decrease a pressure worked on the molds.

BRIEF DESCRIPTION OF THE DRAWINGS

The accompanying drawings show presently preferred embodiments of the invention, in which:

FIG. 2b shows a side view of FIG. 2a;

FIG. 4 shows a mechanism for fixing the mold to the swing arm according to the present invention, further FIG. 4 is a sectional view on a line IV—IV in FIG. 1;

DESCRIPTION OF THE PREFERRED EMBODIMENT

A crimping apparatus has a swing section A for contacting and separating molds, a motor gear section B for driving the swing section A, and a X-Y table section C for adjusting a position of a lower mold 2 (a static mold) against a upper mold 1 (an active mold).

The upper mold 1 is coupled with a swing arm 3, which is a part of the swing section A. The lower mold 2 is fixed on the X-Y table section C, which is disposed on frame 4. The upper mold 1 and the lower mold 2 are disposed in front-rear direction of the apparatus (the front side is left in FIG. 1) at a certain angle. The upper mold 1 is disposed to be in a straight line with the lower mold 2 when they contact to each other. The angle of the mold 1,2 is not limited to a specified angle, but it will be set with consideration of convenience of the operator who stands in front of the apparatus. In this embodiment, the angle is set 45 degrees.

At points of the mold 1,2, there are small grooves in respect to the diameter of a micro needle (an eyeless needle) for positioning it. During crimping the micro needle is disposed perpendicular to a axis of the molds 1, 2.

The swing section A is a mechanism to make the molds 1, 2 contact and separate. This section A comprises a swing arm 3, a pivoting axis 5 which is disposed far enough from a contacting point of the molds 1, 2 and in parallel with a root end section of the micro needle on the lower mold 2. Both ends of the pivoting axis 5 have a conical shape and supported by bearings 6.

Length L2 (shown in FIG. 3) between the contacting point of the molds 1, 2 and the pivoting axis 5 is set to be long enough. This length L2 is not limited to a absolute number, and it can be selected for any length as long as it is relatively long enough for radius R of the pivoting axis (shown FIG. 2 (A)). There is a space for the setting position of pressure adjustment member 23, which is explained later. In this embodiment, the length L2 is set at 100 mm, for example. Although the pivoting axis has a diameter of 8 mm, the supporting radius R becomes 2 mm because it has conical ends 5a. Thus, the ratio of R/L2 is 1/50. The thickness of the pivoting axis 5 is set to be strong enough for the force exerted when cramping a micro needle, changing the molds, maintaining the apparatus, and so on.

Figure 2B:
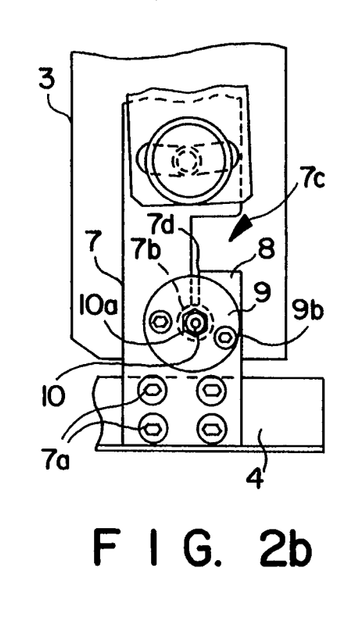

The pivoting axis 5 has length L1 which is long enough for crimping length Lc of the micro needle. As shown in FIG. 2 (A) and (B), the bearings 6 are coupled with column members 7, which are fixed to the frame 4 with bolts 7a. The bearings 6 are respectively inserted in holes 7b of the column members 7. Each column member 7 has a notch 7c and slit 7d, which forms clamping member 8. On the outside of the column member 7, a plate 9 having a female screw 9a is attached to bolt 9b. Bolts 10 with fixing nut 10b are screwed into the female screws 9a. Therefore, by rotating the bolt 10 to move it in a-arrow direction, it is possible to adjust the aperture between the pivoting axis 5 and the bearings 6 to be minimum. Then the bearings 6 are fixed to the column members 7 by clamping them with clamping member 8 with bolts (not shown).

Even though the aperture between the axis 5 and the bearings 6 can be set to a minimum, the aperture will still remain. The aperture causes a parallel discrepancy and a twisting discrepancy. In this embodiment, the aperture is 0.001 mm. Because the pivoting axis 5 is 100 mm long, the maximum twist of the upper mold 1 against the lower mold 2 becomes 1/100000 radian, the maximum discrepancy in a direction of the swing arm 3 becomes 0.001 mm (1 $\mu$m). Compared with the thickness of the micro needle, which is 23 $\mu$m ~ 27 $\mu$m, the discrepancy can be neglected in actual use.

The swing arm 3 is coupled with the central portion of the pivoting axis 5. This swing arm 3 is fixed to the pivoting axis 5 at one end 3a and the other end 3b swings, to which the upper mold 1 is attached. A pressure setting member 23 of the motor gear section B is coupled with mid-portion of the swing arm 3.

A fixing mechanism of the pivoting axis 5 and the swing arm 3 will be explained below.

The swing arm 3 has a hole 3d at one end 3a, which is for holding the pivoting axis 5. A slit 3e is formed between the hole 3d and the outer face of the swing arm 3, which forms a clamping tip 11. By inserting the pivoting axis 5 to the hole 3d and clamping the tip 11 with a bolt 11a, the swing arm 3 can be fixed to the pivoting axis 5.

As explained above, in this embodiment the swing arm 3 is apart from the pivoting axis 5. Of course, the swing arm 3 and pivoting axis 5 can be formed in one body.

Figure 4:
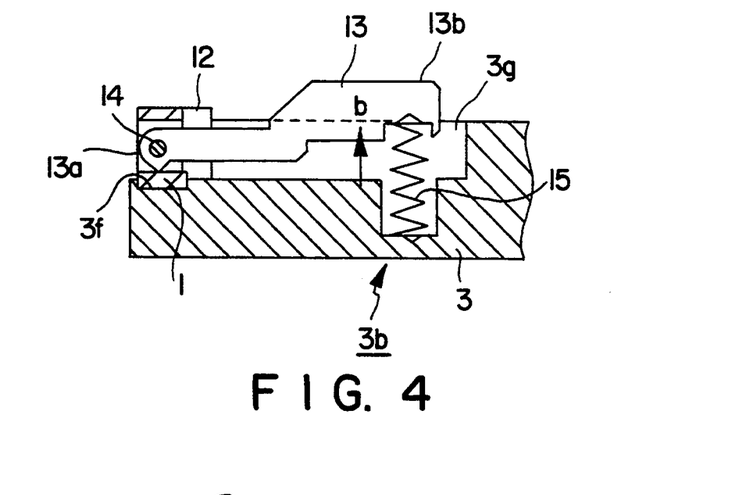

The swing arm 3 is coupled with an upper mold holder 12 at the end 3b, as shown in FIG. 4. A groove 3f for inserting the upper mold 1 and a groove 3g for positioning a clamping lever 13 are also formed at the end 3b. The upper mold holder 12 has a rotating pin 14, to which the clamping lever 13 is pivoted at its end 13a. The other end 13b of the clamping lever 13 is given a pressure in a b-arrow direction shown in FIG. 4 and the end 13a presses the upper mold 1 to fix it to the swing arm 3. The swing arm 3 has a stopping pin 16 above the upper mold 1, which is for obstructing a shift of the upper mold 1 when substantial force is given to the upper mold 1 and the clamping lever 13 fails to fix the upper mold 1.

Figure 5:
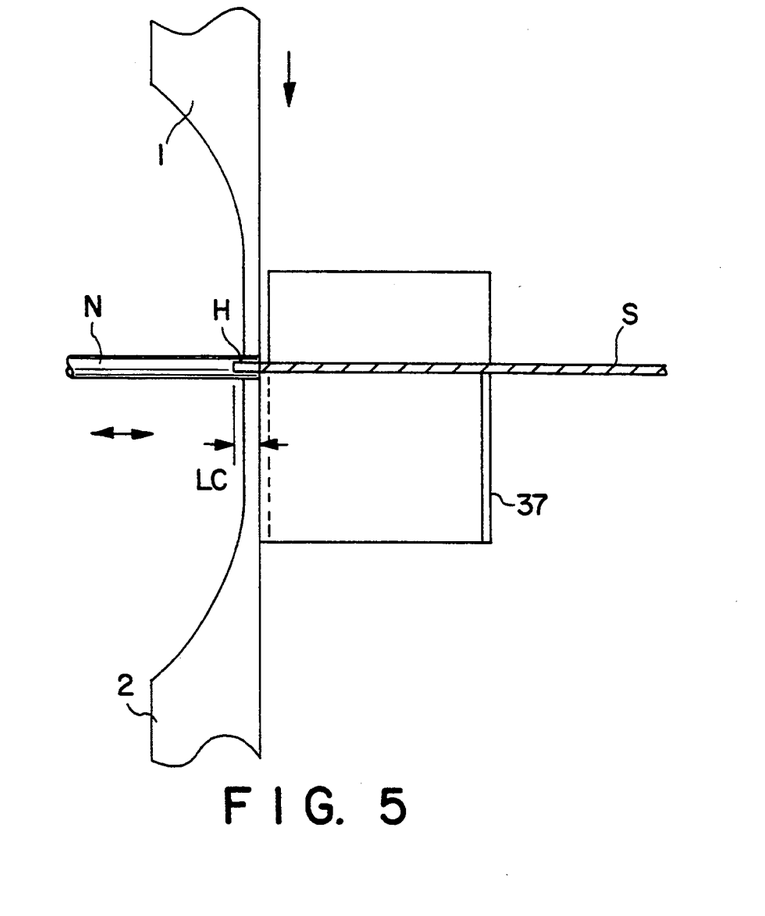
FIG. 5 shows a crimping portion of a crimping apparatus according to the present invention.

As shown in FIG. 5, by rotating the swinging arm 3, the upper mold 1 moves toward the lower mold 2, on which the micro needle N is put. The micro needle N has a hole H at its root end, in which the medical suture S is inserted. When the upper mold 1 comes down, the hole H is pressed between molds 1, 2 to be crushed, and this crushed hole H holds the end of the suture S.

Therefore, sliding portion of the swing section A is the only contacting portion of the pivoting axis 5 and the bearings 6. By forming ends of the pivoting axis 5 conical, and by giving a thrust load to the pivoting axis 5 and the bearings 6, the aperture between them can be set minimum. Thus, when rotating the swing arm 3, the contacting accuracy of the molds 1, 2 is improved.

The frictional resistance F is set by the material of the pivoting axis 5 and the bearings 6, as well as the thrust load on them. The frictional resistance F is a resistance against the rotation of the swing arm 3, which influences the crimping pressure. However, because the ratio of the length L2 of the swing arm 3 to the radius R (L2/R) is small (1/50) in this apparatus, the influence of the frictional resistance F is kept very small. Although the aperture between the pivoting axis 5 and the bearings 6 are tightly set and the frictional resistance F becomes larger, the rotation of the swing arm 3 is not affected by the frictional resistance because of the ratio L2/R. Thus, this apparatus can improve the contacting accuracy and the influence of the frictional resistance can be kept small.

In this embodiment, the ends of the pivoting axis 5 are formed conical-shaped, but this is just one example and other mechanisms, like putting a tapered collar to the pivoting axis with a nut, might be chosen. The pivoting axis 5 could be supported at one end. Namely, the mechanism can be constructed by forming a journal long enough for the crimping length Lc in the pivoting axis 5 and by supporting it with the bearing with a transition fit.

The swinging end of the swing arm 3 is given a force by the weight of the swing arm itself. This force is constant. The swing arm 3 is coupled with a adjusting member 17 for supporting the weight during operation. The adjusting member 17 has a spring 17c disposed between a stay 17a and the swing arm 3. This adjusting member 17 also has adjusting nut 17b for changing the tension of the spring 17c. By using the adjusting member 17, the upper mold 1 can avoid giving strong force to the upper mold 1 during operation of the apparatus.

The swing arm 3 has stoppers 18, 19 for limiting the angle of the rotation of the swing arm 3 as well. By using those stoppers 18, 19, the rotating angle can be set small for avoiding unnecessary movement.

Figure 1:
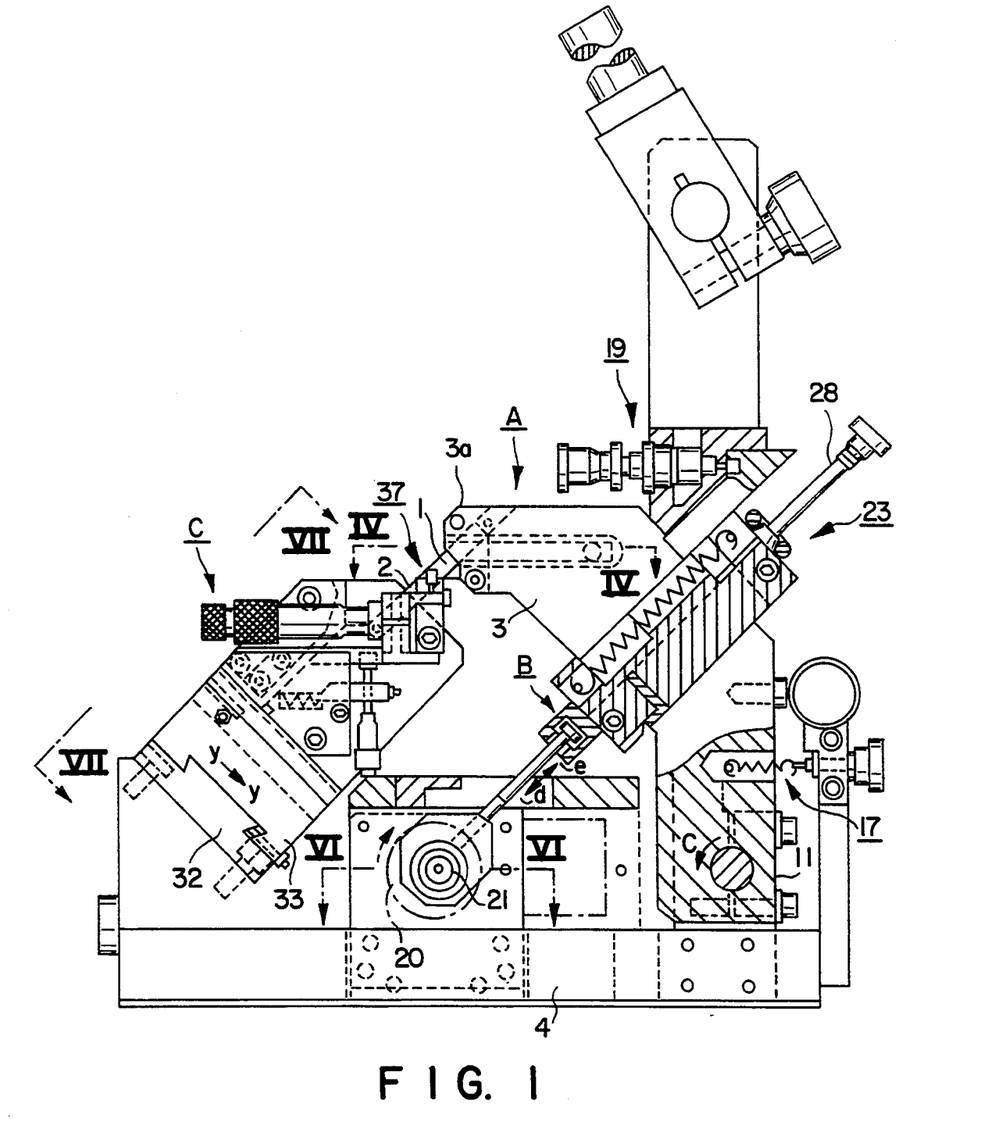
FIG. 1 is a sectional side view of a whole crimping apparatus according to the present invention.

The motor gear section B is a mechanism for moving the swing arm 3 in a c-arrow direction in FIG. 1, namely the crimping direction. This motor gear section B can give an adjusted pressure to the upper mold 1 via the swing arm 3.

This motor gear section B comprises a motor 20, a converting member 21 for changing the rotation of the motor 20 to reciprocating movement, a transfer member 22 for transferring the reciprocating movement from the converting member 21 and the pressure setting member 23 attached to the swing arm 3 for setting the force to the swinging arm.

Figure 6:
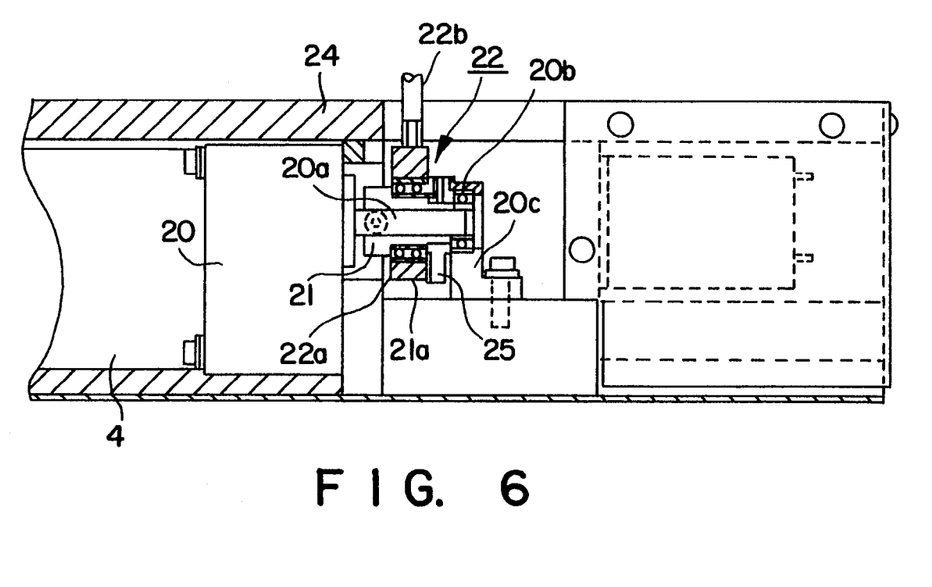
FIG. 6 shows a mechanism of a motor gear of the present invention; a sectional view on a line VI—VI in FIG. 1.

As shown in FIG. 6, the motor 20 is fixed on a motor mount 24 of the frame 4. A reduction motor with a reduction gear might be selected for this motor 20. One end of an axis 20a of the motor 20 is supported by the bearing member 20c comprising a ball bearing 20b.

The axis 20a is coupled with an eccentric collar 21 as the converting member 21 and a transfer plate 22a of the transfer member 22 is attached to the outside of this eccentric collar 21. A projection for contacting micro switch (not shown) is fixed to the top of the eccentric collar 21 to send a signal at each rotation.

The transfer member 22 comprises a transfer plate 22a which is rotation-freely attached to the eccentric collar 21 and a transfer bolt 22b screwed to the transfer plate 22a.

The transfer bolt 22b is rotation-freely inserted into a hole 26a of a hook plate 26. It is constructed that a foot 22c of the transfer bolt 22b is connected to the hole 26a so as to stop the transfer bolt 22b from rotating by the eccentric collar and a head 22d of the transfer bolt 22b is connected to the hook plate 26 to transfer driving force of the motor 20 toward the pressure setting member 23.

When the motor starts, the eccentric collar 21 rotates. Then the transfer bolt 22b reciprocates by the eccentric collar 21 in a d,e-arrow direction in FIG. 1. This movement is transferred to the pressure setting member 23 via the head 22d and hook plate 26. The stroke can be adjusted by changing the connecting length of the transfer bolt 22b and the transfer plate 22a.

The pressure setting member 23 is for adjusting the load given to the swing arm 3, namely to the upper mold 1 by the transfer bolt 22b. This pressure setting member 23 comprises spring 27 having certain spring constant and length, and an adjusting screw 28 for changing the load given to the swing arm 3 by setting initial shrinking length. This embodiment uses two tension springs as the adjusting spring 27. Material, diameter, coiling number and length of the spring 27 are decided by calculating intentional crimping pressure of the upper mold 1, frictional resistance between the pivoting axis 5 and the bearings 6, a resistance in the adjusting member 17 and so on. This spring 27 is disposed inside a hole formed in a direction of the width of the connecting tip 3c of the swinging arm 3 and supported by hooking ends to the fixing members 29, 30 formed at both end of the connecting tip 3c. One fitting member 29 is formed with a hook plate 26 in one body, and it has a pin 29a. A side plate 29b having a longer length than a stroke of the adjusting member 23 (eccentric length of the collar 21) are fixed to the side face of the fixing member 29. The other fixing member 30 also has pin 30a and screw member 30b for an adjusting screw 28. A side plate 30c is fixed to both sides of the connecting tip 3c with bolts 30d. The side plate 30c has the same length as the adjusting member 28. Both ends of the spring 27 are coupled to pins 29, 30.

The side plate 29b, 30c is for guiding a moving direction of the fixing member 29, 30 by contacting to the side of the swing arm 3. The adjusting screw 28 is for adjusting an initial shrinking length of the spring 27 in respect to the frictional resistance between the pivoting axis 5 and the bearings 6, and a difference of the weight between the swing arm 3 and pressing force.

The adjusting screw 28 has a certain length and a certain screw pitch to finely adjust the shrinking length of the spring 27. For making it easy to rotate the screw 28, a rotating wheel 28a is fixed to the screw 28 at its end. This adjusting screw 28 also has a lock nut 28b like a butterfly nut for keeping the initial shrinking length of the spring 27. The adjusting screw 28 is screwed to an female screw 30b of the fixing member 30. The screw 28 is disposed inside the fixing member 30 and its point contacts to the side face of the connecting tip 3c of the swing arm.

As described above, by rotating the adjusting screw 28 to move the fixing member 30 in f,g-arrow direction, it is possible to change the initial shrinking length of the spring 27 before starting the apparatus. Then by using the lock nut 28b, the initial shrinking length of the spring 27 is fixed. After setting the initial shrinking length of the spring 27, as describe above, the eccentric collar 21 can be rotated by starting the motor 20. This rotation is transferred to the transfer bolt 22b fixed to the hook plate 26 via transfer plate 22a to move the transfer bolts 22b in d,e-arrow direction. When a head 22 of the bolt 22b contacts to hook plate 26 by the d-arrow direction movement, the movement is transferred to the hook plate 26 and the fixing member 29. This movement is also transferred to the fixing member 30 via the spring 27, then transferred to swing arm 3 via the adjusting screw 28. The force given to the swing arm 3 applies a force on the upper mold and the force is set by the adjusting member 23.

When rotating the swing arm 3 in c-arrow direction (FIG. 3), the frictional resistance between the pivoting axis 5 and bearings 6 reduce the force of the upper mold 1 as well as the adjusting member 17 which also reduces the force. Thus, the force set by the pressure adjusting member 23 is subtracted from the force given to the upper mold 1. Because the lost force is constant, the micro needle is crimped with constant force.

The pressure setting member 23 might be disposed next to the stopper 19 to guide the moving direction of the fixing member 30. The stopper 19 might have a pointing mark and the fixing member 30 of the pressure setting member 23 might have a scale mark for convenience to show the initial shrinking length of the spring 27.

The swing arm 3 rotates about the pivoting axis 5. Because the movement of the swing arm 3 is very simple, the moving locus of the pointing of the swing arm 3 is stabilized.

The lower mold 2 is mounted to the lower mold holder 31 on x-y table C (FIGS. 1 and 7) which is disposed perpendicular to the moving direction of the upper mold 1. In this table C, x-direction (FIG. 7) is the direction parallel to the micro needle on the lower mold 2 (shown in FIG. 7), and y-direction is the direction perpendicular to the micro needle (shown in FIG. 1).

Figure 7:
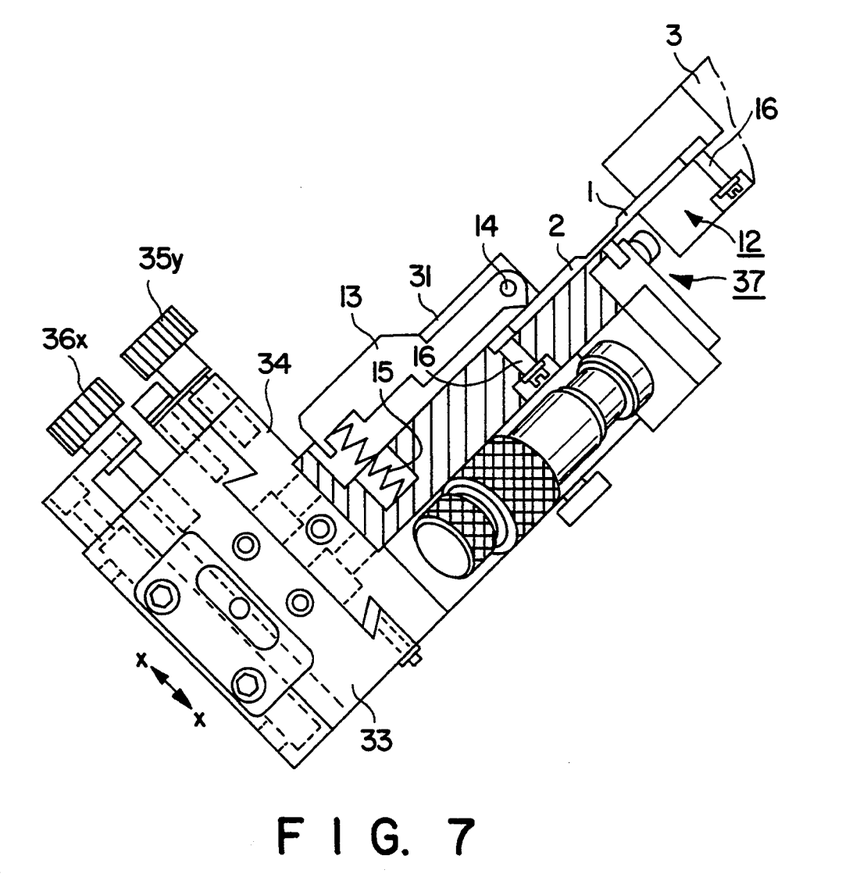
FIG. 7 shows a mechanism to fix a lower mold to a frame according to the present invention; a sectional view on a line VII—VII in FIG. 1.

The x-y table C, comprises a base table 32 mounted on the frame 4 by block 32a, x-table which can shift in x-direction, and y-table which can shift in y-direction. The x-table 33 and y-table 34 respectively have adjusting screw 35x, 35y and fixing screw 36x, 36y for shifting the lower mold 2 to the suitable position by moving the tables 33, 34 and for fixing them at the position. The lower mold holder 31 is mounted on the y-table 34.

A guide member 37 for guiding the point of the suture S is disposed at a certain position next to the lower mold 2. This guide member 37 is used when inserting the end of the suture S into the hole of the micro needle N. The guide member 37 is constructed by combining two guide parts with a clamping member.

As illustrated in FIG. 5, an operator will put a micro needle N on the lower mold 2 and put the upper mold 1 down onto the lower mold 2 to temporarily clamp the micro needle with the weight of the swinging arm 3 only. Then the operator will insert a suture into the hole H at the root end of the micro needle N by using the guiding method 37. When starting the motor gear B, the root end of the micro needle N will be crushed between the molds 1, 2 and the end of the suture S will be attached to the needle N.

By further rotating the motor gear B to separate the molds 1, 2, the operator can get the needle out from the apparatus and put a new a unprocessed needle on the lower mold 2.

The individual components shown in the outline or designated by blocks in the Drawings are well known in the needle crimping arts, and their specific construction and operation are not critical to the operation or best mode for carrying out the invention.

While the present invention has been described with respect to what is presently considered to be the preferred embodiment, it is to be understood that the invention is not limited to the disclosed embodiment. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A crimping apparatus for crimping a root end of an eyeless needle, said root end having an axis, said apparatus comprising,
    a lower mold mounted on a frame and having a crimping surface for crimping the root end of said eyeless needle, said crimping surface arranged to crimp said root end of said eyeless needle so that said root end axis extends along an axis of said crimping surface, said crimping surface having a crimping length as measured along said crimping surface axis, an upper mold mounted on an arm and pivotal on a shaft about an axis towards said lower mold, said upper mold having a crimping surface cooperating with said crimping surface of said lower mold, said crimping surface of said upper mold arranged to crimp said root end of said eyeless needle so that said root end axis extends along said crimping surface axis, said crimping surface of said upper mold having a crimping length as measured along said crimping surface axis, said axis of said shaft extending parallel to said axes of said crimping surfaces and to said axis of the root end of said eyeless needle, said shaft having a length substantially longer than the crimping surfaces as measured along said crimping surfaces' axes, said shaft having conical ends which are journaled in bearings mounted on said frame;

said bearings being movable in the length direction of said axis, whereby the axis can be positioned by adjusting both ends of the bearings.

2. A crimping apparatus according to claim 1, further comprising:
- a motor for moving said arm, and
- a pressure setting member disposed between said motor and said arm for setting crimping force given by said upper mold by changing an initial spring force.

3. A crimping apparatus according to claim 1, wherein said arm temporarily holds said needle between said upper mold and said lower mold with the weight of said arm.

4. A crimping apparatus according to claim 3, further comprising an adjusting spring attached to said arm for changing said weight of said arm put on said upper mold.

5. A crimping apparatus according to claim 1, further comprising a positioning means for shifting and fixing the relative position of said lower mold to said upper mold.

6. A crimping apparatus according to claim 5, wherein said positioning means is a x-y table for moving said lower mold in two directions orthogonal to each direction.

* * * * *